United States Patent
Cumming

(10) Patent No.: US 6,660,036 B2
(45) Date of Patent: *Dec. 9, 2003

(54) COLLARS FOR LENS LOOPS

(75) Inventor: J. Stuart Cumming, Laguna Beach, CA (US)

(73) Assignee: Medevec Licensing B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 10/051,410

(22) Filed: Jan. 18, 2002

(65) Prior Publication Data

US 2002/0065556 A1 May 30, 2002

Related U.S. Application Data

(63) Continuation of application No. 09/756,546, filed on Jan. 8, 2001, now Pat. No. 6,391,056, which is a continuation of application No. 09/419,072, filed on Oct. 15, 1999, now Pat. No. 6,193,750.

(51) Int. Cl.[7] .................................................. A61F 2/16
(52) U.S. Cl. .................... 623/6.43; 623/6.11; 623/6.38; 623/6.45
(58) Field of Search ................................ 623/6.11, 6.38, 623/6.4, 6.43, 6.44, 6.45, 6.51, 615; 606/148, 151, 152, 153, 232

(56) References Cited

U.S. PATENT DOCUMENTS

| 4,298,996 | A | | 11/1981 | Barnet |
| 4,710,195 | A | | 12/1987 | Giovinazzo |
| 4,969,897 | A | | 11/1990 | Kalb |
| 5,476,514 | A | | 12/1995 | Cumming |
| 6,391,056 | B2 | * | 5/2002 | Cumming ............... 623/6.43 |
| 6,409,763 | B1 | * | 6/2002 | Brady ..................... 623/6.43 |

FOREIGN PATENT DOCUMENTS

| EP | 0 496 022 A | 7/1992 |
| WO | WO 97 12564 A | 4/1997 |

* cited by examiner

*Primary Examiner*—Corrine McDermott
*Assistant Examiner*—Kamrin Landrem
(74) *Attorney, Agent, or Firm*—Orrick, Herrington & Sutcliff LLP

(57) ABSTRACT

Collars are disposed on loops of intraocular lenses for improved fixation of loops in rims of capsular bags of eyes. A collar may preferably be positioned on an outer portion of a loop and retained on the loop by an enlarged end portion of the loop.

25 Claims, 2 Drawing Sheets

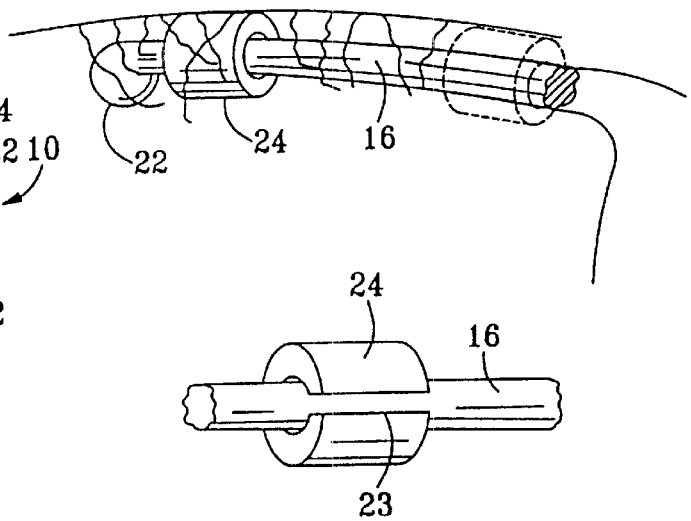
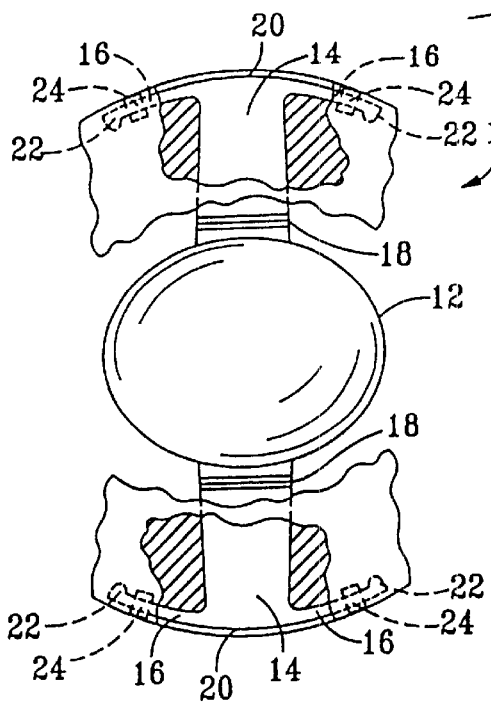
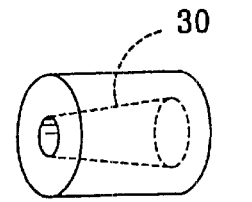
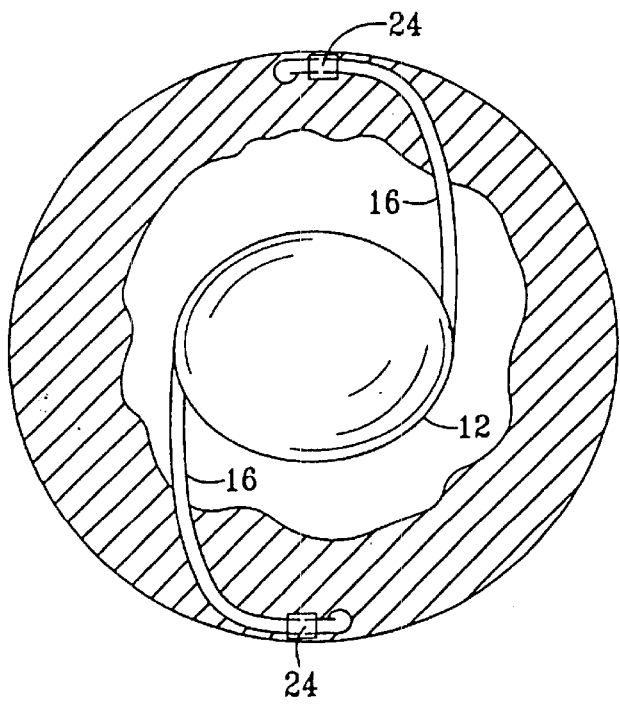

COLLARS FOR LENS LOOPS

RELATED APPLICATIONS

This application is a continuation of U.S. patent application Ser. No. 09/756,546, filed Jan. 8, 2001, now U.S. Pat. No. 6,391,056 which is a continuation of U.S. patent application Ser. No. 09/419,072, filed Oct. 15, 1999, U.S. Pat. No. 6,193,750.

BACKGROUND AND SUMMARY OF THE INVENTION

In the implanting of intraocular lenses in human eyes, particularly where accommodation is to be provided, it is important that loops of lenses be fixated within the rim of the capsular bag of the eye to maintain correct, accurate movement of the optic under the action of the ciliary muscle.

As is known in the art, loops, haptics, etc., disposed in the capsular bag rim, are intended to become fixated by fibrosis developed therein following surgical removal of a portion of the anterior capsular bag.

It is possible, although rare, that loops and certain other lens features engaged in the rim of the capsular bag may lose some degree of fixation or undergo some disengagement from the capsular bag rim. Lenses in which such problem might possibly arise include the well-known type of lens wherein arcuate loops extend oppositely from an optic; the lenses of Applicant's pending application, Ser. No. 08/858,978 entitled "Accommodating Intraocular Lens Having T-shaped Haptics"; and Applicant's pending application Ser. No. 08/947,113 entitled "Intraocular Lenses With Fixated Haptics".

The present invention provides collar components for positioning on loops of lenses in the rim of the capsular bag of the eye, thus to enhance engagement of the loop and collar in the bag rim.

In a typical or preferred utilization of the collar on the invention, the collars are disposed on a lens comprising an optic having two haptics extending therefrom, at least one loop extending from each haptic, with the loops having enlarged end portions, whereby tubular collars disposed on the loops are retained thereon by enlarged end portions.

BRIEF DESCRIPTION OF THE DRAWINGS

FIG. 1 is an elevational view of a lens having haptics with loops extending oppositely and with collars of the invention thereon;

FIG. 2 is a fragmentary perspective view of a loop with collar thereon and disposed in the rim;

FIG. 3 is a fragmentary perspective view which shows a collar having a slit therein and disposed on a loop;

FIG. 4 is a perspective view of a collar with features thereon for enhanced engagement in the rim portion of a capsular bag;

FIG. 5 is a perspective view of a collar of the invention having a frusto-conical lumen therein;

FIG. 6 is an enlarged sectional view of a lens with oppositely disposed arcuate loops extending from an optic into engagement with the rim portion of a capsular bag and having collars thereon;

DESCRIPTION OF THE PREFERRED EMBODIMENTS

Figure 7:
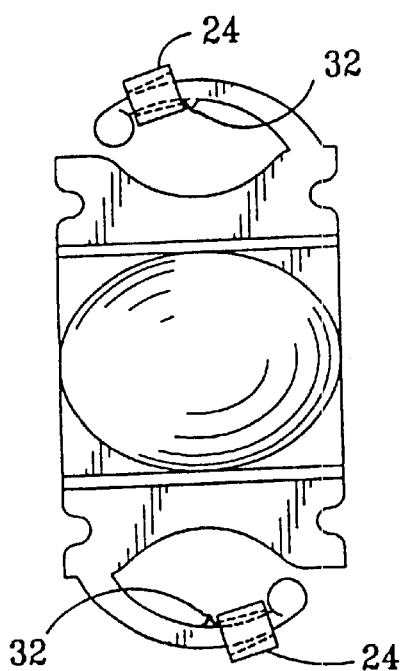
FIG. 7 shows collars of the invention disposed on loops extending from haptics of a lens.

Referring to FIG. 1 of the drawings, a preferred form of intraocular lens 10 with which the collars of the invention may be utilized, has flexible haptics 14 extending laterally oppositely from an optic 12. The haptics are plate haptics having arcuate outer edges. The loops, when unrestrained, are somewhat less curved in configuration than shown. The lens, including the optic, haptics, and loops are preferably formed of resilient, semi-rigid material, such as silicone, acrylic or hydrogel.

As is well known in the art, an intraocular lens, such as that of FIG. 1, is implanted in the capsular bag of an eye after removal of the natural lens. The lens is inserted into the capsular bag via a generally circular opening cut in the anterior capsular bag of the human lens, and through a small opening in the cornea or sclera.

With the outer ends of the haptics positioned in the cul-de-sac of the bag, as shown, the loops 16 are resiliently urged in close proximity with the bag cul-de-sac, the loops being deflected in the configuration shown.

Knobs 22 are defined on the outer end portions of the loops for improved securement in the capsular rim or cul-de-sac by engagement with fibrosis which develops in the capsular bag following the surgical removal of the central portion of the anterior capsular bag.

A collar 24 of the invention is disposed on each loop 16 in positions shown when the lens is positioned in the eye. The collars are preferably fabricated of a relatively hard material, such as polyimide, PMMA, or nylon, whereas the loops are typically formed of a flexible material, such as silicone, acrylic or hydrogel, as earlier mentioned.

Collars may be installed and disposed on loops by different procedures. A collar may be provided with a longitudinal slit 23 (see FIG. 3) to enable it to be deformed or spread open during positioning about a collar. Another procedure disposing a collar on a loop is to dispose a loop in an appropriate recess in a mold, then molding the loop to extend within and through the collar. Another procedure is to fabricate the loop of a hydrogel or acrylic material, slide the collar on the loop, then hydrolyze the loop, thus expanding the ioop and the knob thereon, whereby the unexpanded loop is retained by the enlarged knob at the end of the loop.

Referring to FIGS. 4 and 5, a collar of the invention may incorporate various features for enhancement of fixation in the capsular bag. Such features may include knurling indicated at 26, annular ridges or rings 28 and a frusto-conical lumen or passage 30 in a collar.

A collar on a loop does not interfere with the stretchability of a loop, loop elasticity enables a loop to flex and stretch while the collar is engaged thereabout and in the rim of a capsular bag for fixing the lens in the capsular bag. The collar is positioned on an outer portion of a loop in proximity to a knob at the end of the loop in the procedure of inserting the lens into the eye, and remains so positioned after fibrosis is complete. The knob retains the collar on the loop to prevent the loop from slipping from the collar. As stated, the collar provides improved fixation in the peripheral rim or cul-de-sac of the capsular bag. To aid in retaining the collar adjacent the knob on the end of the loop, a small protrusion 32 may be defined on a loop, as shown in FIG. 7, the protrusion being sized to allow a collar to be slipped thereover after the loop is formed in the manufacture of the lens.

Figure 8:
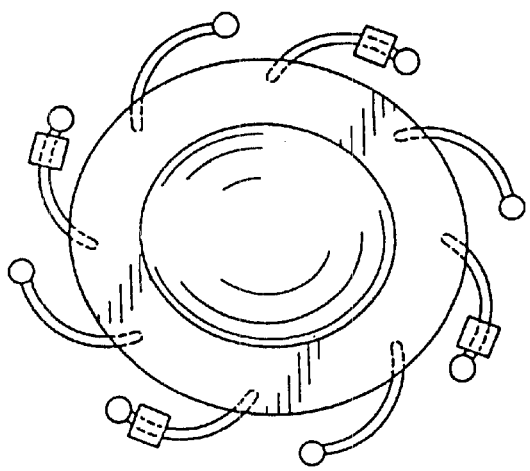
FIG. 8 is an elevated view showing collars of the invention on loops extending from the outer edge of an annular haptic.

FIGS. 6 to 8 show certain of the various forms of lenses with which the collars of the invention may be utilized. FIG.

6 illustrates a type of lens well known in the art, wherein loops extend arcuately from an optic and into engagement with the capsular rim of an eye, with collars of the invention adjacent to knobs at the ends of the loops. FIG. 7 shows a lens having plate haptics and arcuate loops, with protrusions 32, extending from respective edge portions of the haptics transversely across the haptics, with collars thereon retained by knobs. FIG. 8 shows a lens having an annular plate haptic disposed about an optic, and a plurality of loops extending arcuately therefrom with collars of the invention retained by knobs on the ends of the loops.

Thus there have been shown and described collars for lens loops which fulfill all the objects and advantages sought therefor. Many changes, modifications, variations and other uses and applications of the subject invention will, however, become apparent to those skilled in the art after considering this specification together with the accompanying drawings and claims. All such changes, modifications, variations and other uses and applications which do not depart from the spirit and scope of the invention are deemed to be covered by the invention which is limited only by the claims which follow.

I claim:

1. A collar for an intraocular lens with loops for engagement in the capsular bag of the eye, said collar comprising:

a tubular-shaped body made of an optical material of a size to fit within the capsular bag of the eye, and said body having an open passage longitudinally disposed throughout said body.

2. The collar of claim 1, wherein said optic material is made from polyimide, PMMA, or nylon.

3. The collar of claim 1, wherein said body has a longitudinal slit.

4. The collar of claim 1, wherein the surface of the body is knurled.

5. The collar of claim 1, wherein the body has annular ridges or rings.

6. The collar of claim 1, wherein the passage is a frusto-conical lumen.

7. An intraocular lens comprising:

a lens body having an optic, said lens body, having at least two haptics extending from the periphery of said lens body, at least one loop projecting from said at least two haptics, and at least one collar disposed about at least one loop.

8. The lens of claim 7, wherein said at least one loops having an enlarged outer end portion.

9. The lens of claim 8, wherein said enlarged outer end portion is a knob.

10. The lens of claim 7, wherein said at least one collar is disposed about the loop and the loop and knob material is expanded by hydration, whereby the collar is retained on the loop by an enlarged knob.

11. The lens of claim 7, wherein said at least one loop has one or more raised surfaces to retain said collar on said loop.

12. The lens of claim 7, wherein said at least one collar is slidably disposed about at least a portion of said at least one loop.

13. The lens of claim 7, wherein said at least one loop is flexible.

14. The lens of claim 7, wherein said at least one collar is fabricated of harder material than the material of said at least two haptics.

15. The lens of claim 7, wherein said at least one collar is made from polyimide, PMMA, or nylon.

16. The lens of claim 7, wherein said at least one loop is made from silicone, acrylic, hydrogel, or an optic material.

17. The lens of claim 7, wherein said at least one collar is tubular.

18. The lens of claim 7, wherein said at least one collar has a longitudinal slit.

19. The lens of claim 7, wherein said at least two haptics are plate haptics extending oppositely from said lens body.

20. An intraocular lens comprising:

a lens body having an optic, said lens body having flexible haptics extending laterally from the optic, at least one loop projecting from said haptics, and at least one collar disposed about the loop.

21. The lens of claim 20 wherein the haptics are plate haptics extending oppositely from the optic.

22. The lens of claim 21, wherein a loop projects from each of the haptics, and at least one collar is disposed about each loop.

23. The lens of claim 22 where each collar is tubular.

24. The lens of claim 22 wherein the collars each have a longitudinal slit.

25. The lens of claim 22 wherein collars are slidably disposed about at least a portion of the loops, and wherein the loops are slidable relative to the collars during vision accommodation.

* * * * *